US006945987B2

United States Patent
Beard et al.

(10) Patent No.: US 6,945,987 B2
(45) Date of Patent: Sep. 20, 2005

(54) PATIENT COOLING SYSTEM

(75) Inventors: Mark Beard, San Antonio, TX (US); David Whyte, Wareham (GB); Peter Stacy, Ferndown (GB); Chris Coward, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 260 days.

(21) Appl. No.: 10/290,938

(22) Filed: Nov. 8, 2002

(65) Prior Publication Data

US 2004/0093050 A1 May 13, 2004

(51) Int. Cl.[7] .................................................. A61F 7/00
(52) U.S. Cl. ...................... 607/104; 607/108; 607/114
(58) Field of Search .................. 607/96, 104, 107–108, 607/114; 5/421; 600/21, 22

(56) References Cited

U.S. PATENT DOCUMENTS

| | | | |
|---|---|---|---|
| 2,104,589 A | * | 1/1938 | Hartman ................ 128/204.15 |
| 3,283,520 A | | 11/1966 | Donohue et al. |
| 3,999,541 A | * | 12/1976 | Tabor ..................... 128/203.12 |
| 4,170,998 A | | 10/1979 | Sauder |
| 4,506,511 A | | 3/1985 | Cameto et al. |
| 4,638,519 A | | 1/1987 | Hess |
| 4,660,388 A | | 4/1987 | Greene |
| 5,044,364 A | | 9/1991 | Crowther |
| 5,081,339 A | | 1/1992 | Stine |
| 5,699,570 A | | 12/1997 | Wilkinson et al. |
| 5,749,109 A | | 5/1998 | Kappel |
| 5,817,147 A | | 10/1998 | Wolf |
| 6,210,427 B1 | | 4/2001 | Augustine et al. |
| 6,282,737 B1 | | 9/2001 | Vrzalik |
| 6,730,115 B1 | * | 5/2004 | Heaton ....................... 607/104 |

FOREIGN PATENT DOCUMENTS

| | | |
|---|---|---|
| EP | 0164086 | 3/1982 |
| FR | 2754167 | 4/1998 |
| GB | 2263872 A | 8/1993 |
| WO | PCT/KR93/00090 | 4/1995 |
| WO | PCT/GB97/01344 | 11/1997 |
| WO | PCT/GB99/03688 | 5/2000 |

* cited by examiner

Primary Examiner—Roy D. Gibson

(57) ABSTRACT

A patient cooling system comprises a patient enclosure or tent having a coaxial hose connection to a re-circulating air-cooling system. The hose comprises an inner tube to introduce air into the enclosure and an outer tube for the return air. The patient cooling system further comprises a patient-supporting mattress comprising a plurality of inflatable compartments extending transversely across the width of the mattress, which can also be supplied with cooled air. The compartments can be alternately pressurized for pressure relief therapy. Moreover, the compartments can be pressurized either with relatively low pressure cold air from the air cooling system, or with higher pressure air which acts to support the patient, but provides relatively less cooling effect. Radially collapsible, sleeved openings in the tent panel enable connection of conduits or patient care lines to the patient.

16 Claims, 5 Drawing Sheets

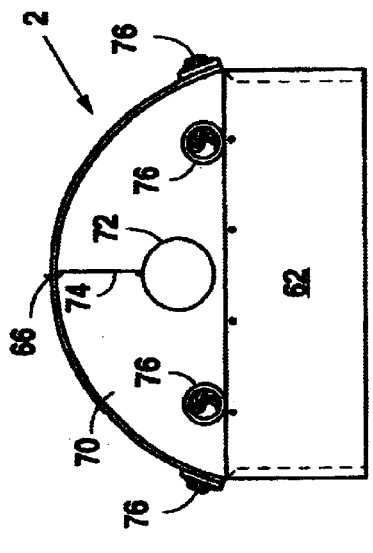
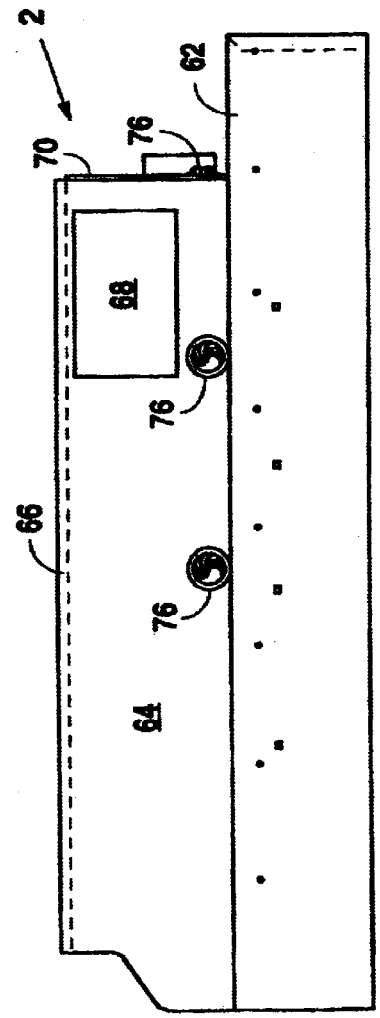
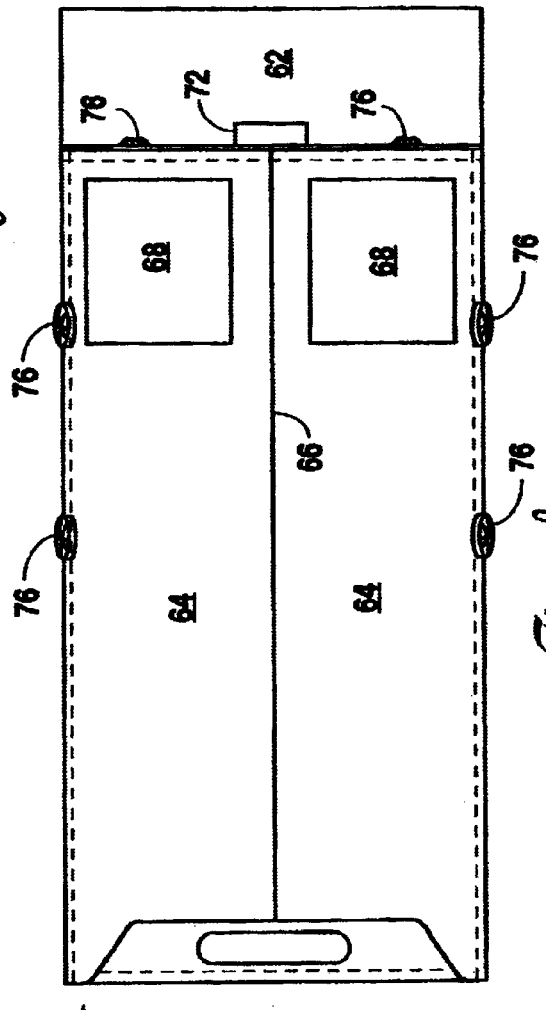
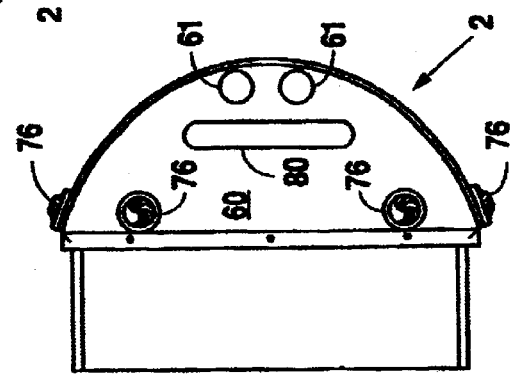

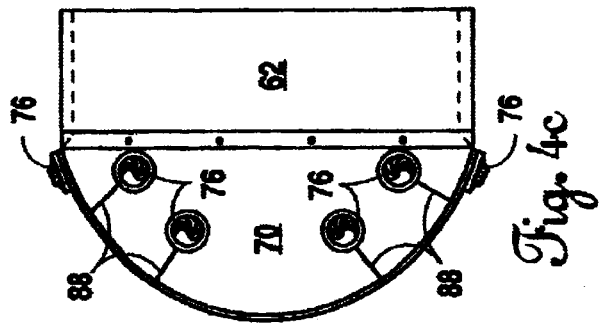
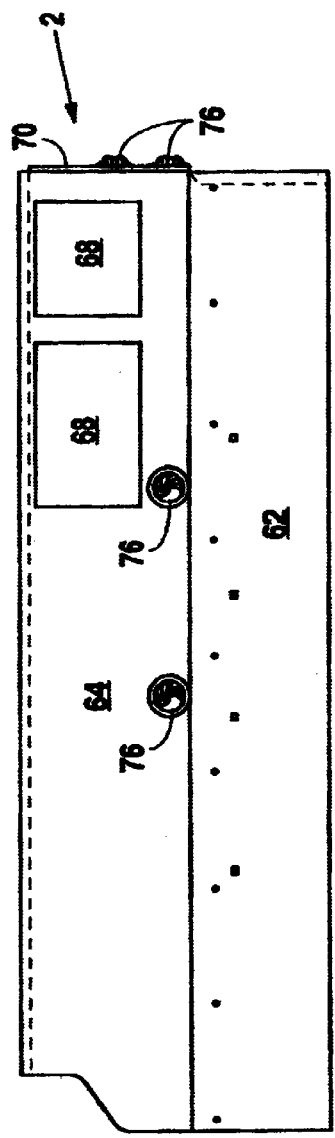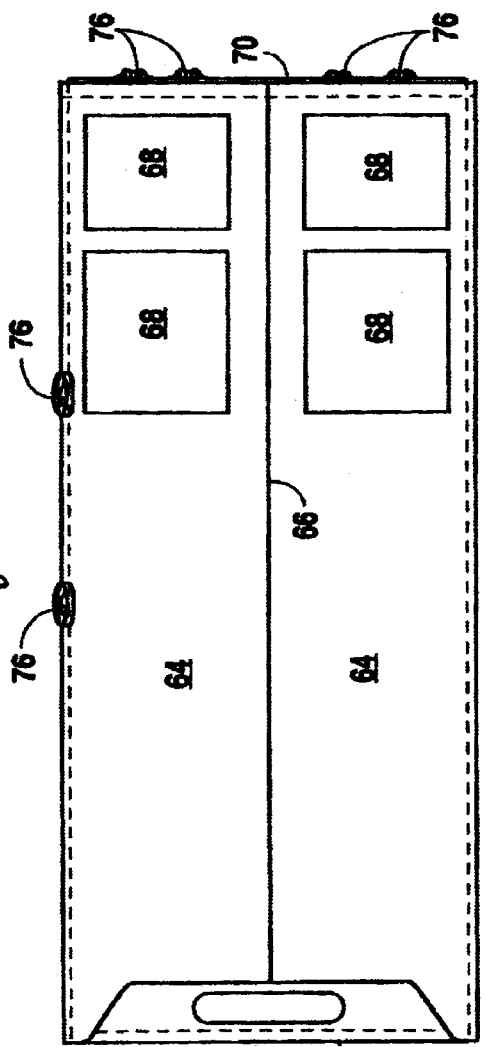

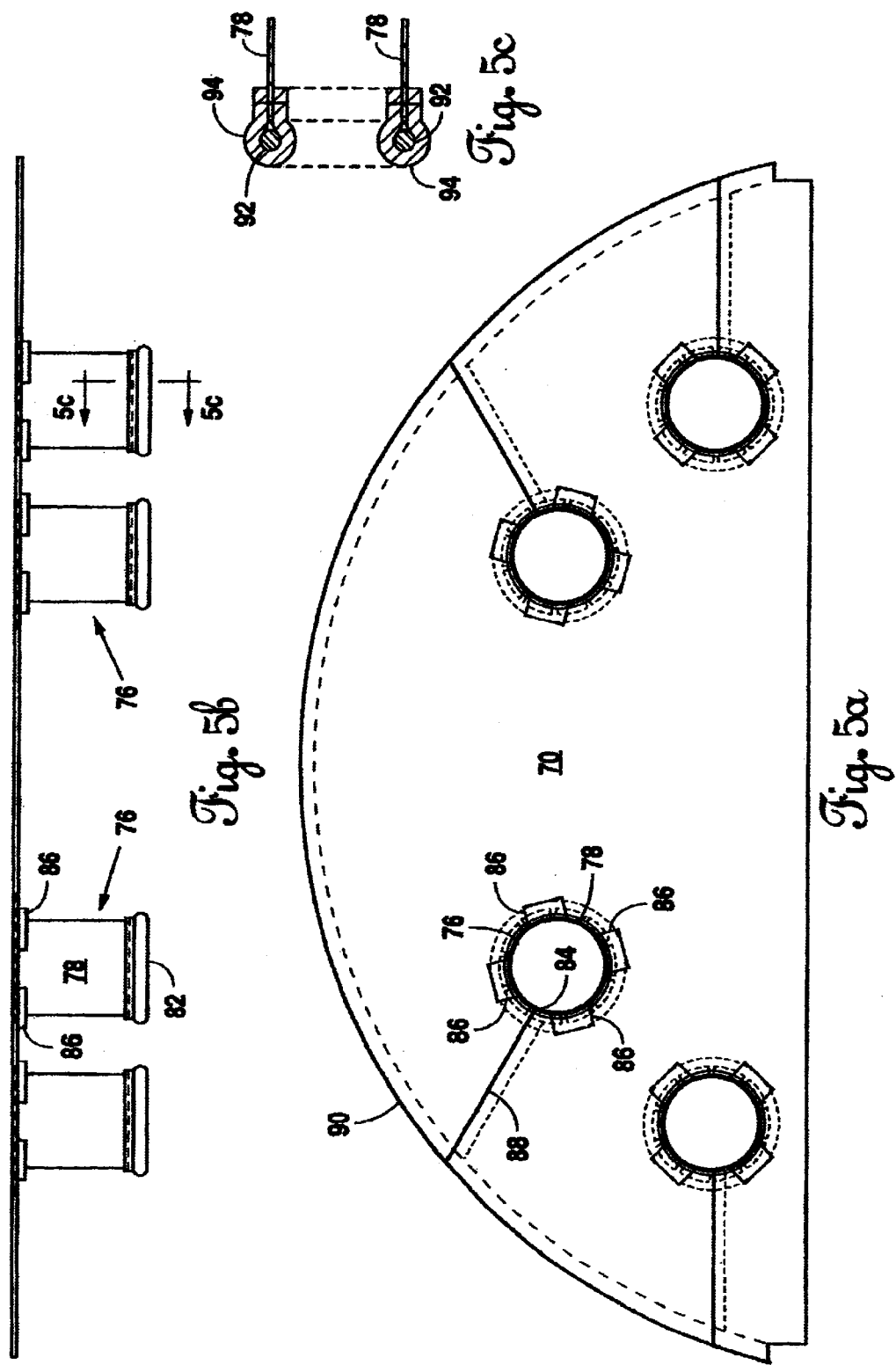

PATIENT COOLING SYSTEM

FIELD OF THE INVENTION

This invention relates generally to systems for cooling a person for therapeutic purposes. More particularly, this invention relates to an enclosure or tent and support system for a patient who is to be cooled to a temperature below normal body temperature.

BACKGROUND

International patent applications published under WO 97/42919 and WO 00/27323, which are incorporated herein by reference for all purposes, describe systems for rapidly cooling a patient to a temperature a few degrees below normal blood temperature, e.g. in the range of about 32 to 34 degrees Celsius. This clinical procedure has been used with some success in reducing brain damage to cardiac or stroke patients as a result of reduced flow of oxygenated blood.

SUMMARY OF THE INVENTION

The present invention provides an improved patient cooling system, which, according to a first feature of the invention, comprises an enclosure or tent having an inlet connected to an air cooling system, and an outlet which is connected to re-circulate exhaust air back to the inlet of the cooling system in order to minimize energy losses. Preferably, the enclosure is arranged so that it can be used on a variety of patient support devices such as mattresses, including support devices mounted in an ambulance fitted with a suitable source of cold air.

Preferably, the enclosure is connected to a cooling system that includes an inlet for ambient air, a main blower that supplies air to the enclosure via the cooling section of a refrigeration system, and a re-circulation duct that connects an outlet from the air tent to the inlet side of the main blower.

Preferably the air inlet, main blower, and cooling section are all embodied in a single housing that is connected to the air tent through a dedicated hose set. Preferably the hose set is coaxial, and includes an inner tube for the inlet air to the enclosure surrounded by an outer tube for the return air. In this way, the outer air jacket advantageously isolates and insulates the colder inner tube from the ambient temperature.

Preferably, a valve is included in the return path to enable the proportion of re-circulated air to be varied, in accordance with operational requirements.

Preferably, the air tent is also provided with a separate outlet to the atmosphere, including a vane type valve to control the exhaust flow, which allows independent control of the pressure inside the enclosure. In this way it is possible to maintain the pressure within the preset limits even if the enclosure is subject to variable leakage.

Preferably, the patient is supported on a mattress system comprising a plurality of inflatable compartments, which can also be supplied with cooled air. Preferably, the compartments comprise elongate members that extend transversely across the width of the mattress, and can be alternately inflated to avoid any particular regions of the patient's body from being subjected to high pressure continuously.

According to a further feature of the invention, there is provided a patient support mattress comprising a plurality of transversely extending inflatable compartments, which are so arranged that each compartment can be alternately pressurized, either with relatively low pressure cold air, which assists in cooling the patient but provides relatively little support, or with higher pressure air which acts to support the patient, but provides relatively less cooling effect.

Preferably the mattress is connected into the re-circulating air supply system of the cooling enclosure, and may be provided with an additional blower to boost the pressure, for its high pressure supply.

According to a still further feature of the invention there is provided an air tent or enclosure for enclosing a patient in a controlled environment, comprising a plurality of panels of flexible material, and having an opening with releasable fastener means to enable a patient to be enclosed, at least one panel including an aperture or apertures to allow the passage of a duct or pipe to communicate with the interior of the enclosure, the aperture comprising a radially collapsible sleeved opening having a split along the side of the sleeve which communicates with a further split in the panel for introduction of the conduit, the sleeve being flexible and being adapted to be tightened around the conduit.

Preferably the outer edge of the sleeve is provided with a ring of hook or loop covered attachment material, which is adapted to cooperate with inter-engageable loop or hook material on the panel around the base of the sleeve, whereby the sleeve can be secured tightly around the conduit after it has been placed in position, by twisting the sleeve around the conduit and pressing the ring of material against the co-operating material on the panel.

Preferably the outer edge of the sleeve is also reinforced with a "split ring" of a resilient material such as aluminum. The split ring maintains the sleeve in a generally circular configuration as it is closed around the conduit and maintains the edge of the sleeve in continuous contact with the surface of the conduit.

These and other aspects and features of the present invention will be readily apparent to those skilled in the art from the following detailed description taken in conjunction with the annexed sheets of drawings, which illustrate the invention.

BRIEF DESCRIPTION OF THE DRAWINGS

FIG. 3a is a side elevation of a first type of patient enclosure.

FIG. 3b is a plan view of the patient enclosure of FIG. 3a.

FIG. 3c is an end elevation of the enclosure of FIG. 3a.

FIG. 3d is an alternate view of the end elevation of the enclosure of FIG. 3a.

FIG. 4a is a side elevation of a second type of patient enclosure.

FIG. 4b is a plan view of the enclosure of FIG. 4a.

FIG. 4c is an end elevation of the enclosure of FIG. 4a.

FIG. 5a is an enlarged view of the end panel of FIG. 4c.

FIG. 5b is a plan view of the end panel of FIG. 5a.

FIG. 5c is a detailed view of a cross-section through part of the structure of FIG. 5a.

DETAILED DESCRIPTION

Based on the description and illustrations provided herein, the many benefits provided by the invented structure and methods of utilization are apparent. These described benefits, as well as those that are inherent to those skilled in the art, fall within the scope of the invention of the present patent application as limited only by the claims appended hereto.

Figure 1:
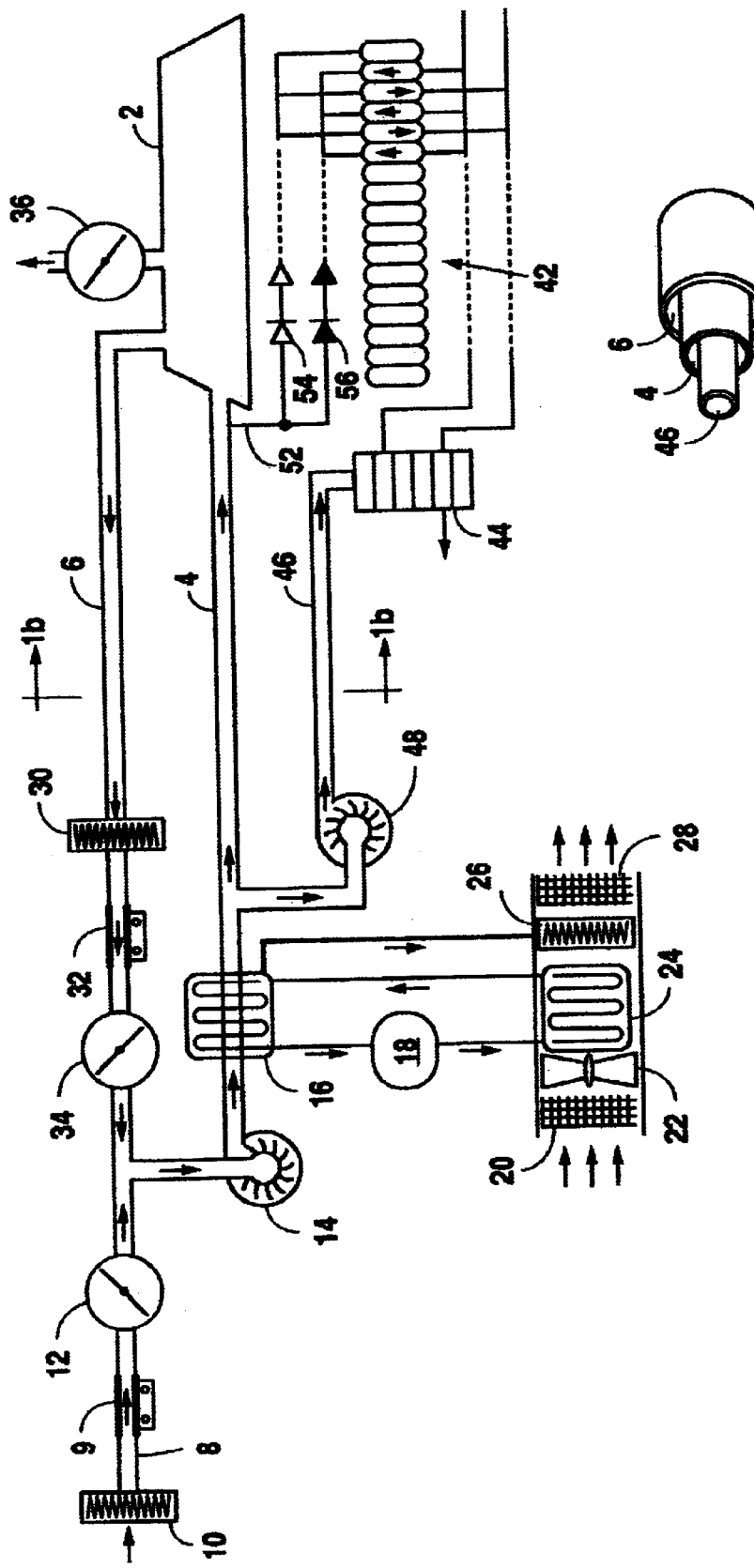
FIG. 1a is a schematic diagram of a patient cooling system according to the invention.
FIG. 1b is a partial cross-section view of the coaxial hose set according to the invention.

Referring to the drawings, FIG. 1a illustrates the general layout of a patient cooling system in accordance with the invention, comprising an air tent 2 forming an enclosure with a tent inlet duct 4 and a tent outlet duct 6. The air tent 2 is preferably constructed from panels of fabric material, as described in more detail below.

The air tent 2 is supplied with cool air through an air inlet duct 8, with a system intake filter 10, an intake flow sensor 9, and an intake valve 12 comprising a movable vane that communicates with a main blower 14. This pressurizes the air, and it then is passed through a heat exchanger 16, which comprises the evaporator section of a refrigeration circuit. The refrigeration circuit further comprises a compressor 18 and a condenser 24, which is provided in a conventional fashion with a condenser fan 22 having a condenser intake filter 20, a wick 26 for absorbing condensate drain from the evaporator section, and an outlet air filter 28.

Having passed through the heat exchanger 16 and thus being cooled, the air passes into the enclosure of the air tent 2 via the tent inlet duct 4, circulates past the patient, and leaves the enclosure via the tent outlet duct 6. The outlet duct 6 is connected by means of a re-circulation filter 30 to a re-circulation flow sensor 32 and a re-circulation valve 34 comprising a vane that can be moved in order to control the proportion of re-circulated air.

The air tent 2 is also provided with a vane type exhaust valve 36 that enables the pressure inside the air tent 2 to be independently controlled. In this way, the proportion of re-circulated air and the internal temperature of the air tent 2 can be controlled without unduly increasing or decreasing the total pressure inside the enclosure.

The apparatus also includes a patient-supporting mattress, indicated generally at 42 in FIG. 1a, which comprises a plurality of inflatable compartments or cells to which air is supplied through an arrangement of servo valves 44 which are connected to the cooling circuit by a conduit 46 containing a further blower 48. As illustrated in FIG. 1a and FIG. 1b, the conduit 46 is incorporated in a coaxial hose set, forming a central core thereof, so that the air passing through the conduit 46 is insulated from the ambient temperature by the outer coaxial passageways of the hose set that comprise tent inlet duct 4 and tent outlet duct 6.

Figure 2:
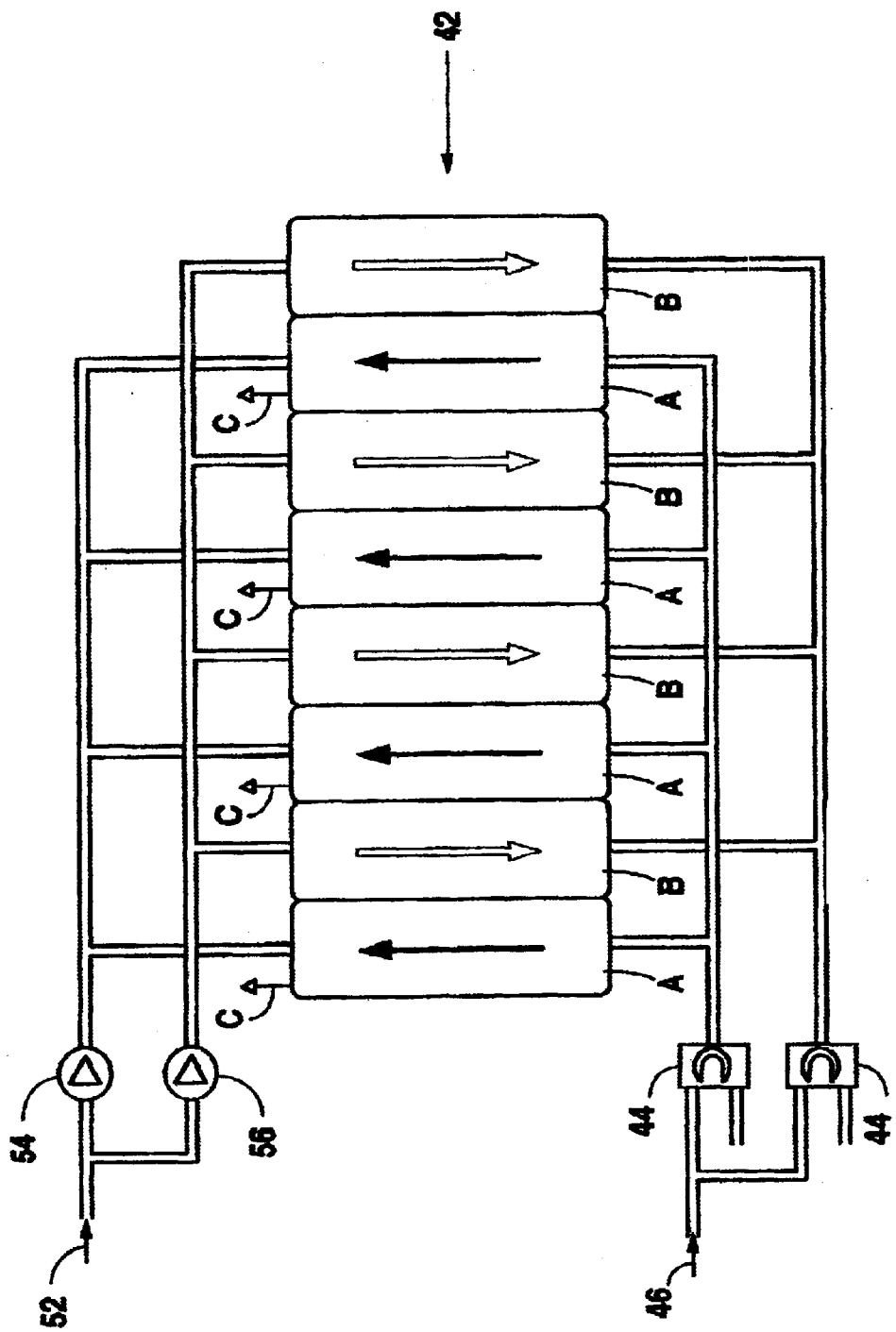
FIG. 2 is a schematic diagram of a patient support mattress having an air flow control system.

FIG. 2 illustrates in more detail how air is supplied to the mattress 42, so that alternate cells are pressurized with high and low pressure air in successive cycles. As shown, there are two interleaved sets of cells or compartments A and B, both of which are connected continuously to a source of cold air at low pressure by means of non-return valves 54 and 56 respectively. In the general arrangement of FIG. 1a, these will normally be connected via line 52 to the tent inlet duct 4 which supplies the air tent 2, and will therefore provide little supporting effect for the patient (being at low pressure) but will have fairly substantial cooling capacity.

The high pressure air supply through conduit 46 driven by the blower 48 (as described above with reference to FIG. 1a) is connected to each set of cells A or B, by a respective servo valve 44, and these are activated alternately so that during a first cycle, all cells A are inflated to a high pressure so as to support the patient while cells B are connected to the tent outlet duct 6 for re-circulation. A controlled amount of leakage is of course permitted through the fabric of each cell, as indicated by arrow C, since the high pressure air cannot escape via the non-return valves 54, 56 (as shown in FIG. 1a and FIG. 2). Since the high pressure air supply via conduit 46 has been subjected to greater pressurization, it is, of course, at a somewhat higher temperature than the low pressure supply, and thus, primarily performs a supporting function rather than a cooling function for the patient's body.

At the same time, however, the cells B are receiving the supply of colder air via line 52 at relatively low pressure, so these cells primarily provide a cooling function rather than a supporting function.

At the next cycle, the high pressure air supply is shut off from the cells A, by operating their respective servo valve 44 and instead, they are connected to the tent outlet duct 6 for re-circulation so that they now act primarily to provide cooling, as passageways for the cold air supply via line 52. At the same time, the cells B are connected to the high pressure supply, so as to take over the patient supporting function, in the same way, as described above for the cells A in the previous cycle.

In this way, each region of the patient's body is alternately supported by the high pressure, or subjected to cooling, rather than being continuously subjected to high pressure.

FIG. 3a illustrates the patient enclosure system in more detail, and as shown, this comprises a generally semi-cylindrical fabric structure, having a base portion (not visible in the Figure) that is supported on a mattress cover 62 enclosing a mattress structure of the kind described above with reference to FIG. 2.

As can be seen from the plan view of FIG. 3b, the upper or covering portion of the enclosure comprises a pair of elongate flaps 64 whose adjoining edges can be connected with a Velcro® type seal (i.e., separable complementary hook and loop fasteners) or similar seal 66, each flap being formed with a flexible, transparent inspection panel 68. A head end panel 70 (FIG. 3c) is formed with an aperture 72 for the neck of the patient, to allow the patient's head to protrude from the enclosure, and this aperture 72 is connected to the circular edge of the head end panel 70, by means of a slit 74 to facilitate the process of positioning the patient's neck. This slit is also provided with a Velcro type or similar seal 66 along its adjacent edges, for subsequent closure.

The air tent 2 is also provided with a series of specially adapted apertures 76, for the entry of various conduits and connectors, as will be described in more detail below, while the foot end 60 (FIG. 3d) is provided with a pair of air input ports 61 for air input ducts, as well as a recirculation aperture 80 for connection to re-circulation and pressure relief valves.

FIGS. 4a, 4b, and 4c illustrate a "full enclosure" version of the system of FIGS. 3a, 3b, 3c, and 3d, in which, as depicted in FIGS. 4a and 4b, the enclosure is longer so as to enclose the patient's head. This version includes additional transparent inspection panels 68 in the head region to allow the patient external vision. In this case, of course, the head end panel 70 does not include a neck aperture.

FIGS. 5a and 5b illustrate the arrangement by which pipes and conduits are passed through the walls of the air tent 2, with minimum air leakage. Each conduit aperture 76 is provided with a radially collapsible tubular sleeve 78 made of flexible material such as fabric. The tubular sleeve 78 is stitched into the head end panel 70 in the arrangement shown in FIG. 5a and projects from the wall as shown in FIG. 5b. The outer edge of the tubular sleeve 78 is reinforced with a split aluminum anchor ring 92 (FIG. 5c) having a covering of Velcro type material 94 stitched around it. Thus the Velcro-covered ring shown in FIG. 5b forms a reinforced sleeve rim 82 at the outer end of the tube to maintain the tubular sleeve 78 in a generally circular configuration as it is closed around the conduit. This reinforced sleeve rim 82, as well as the tubular sleeve 78 itself, is formed with corresponding splits 84 which enable the tubular sleeve to be closed around a conduit, as explained in more detail below.

Continuing in FIG. 5a, four Velcro type "loop" pads 86 stitched to the head end panel 70 of the air tent 2 surround the tubular sleeve 78. The panel itself includes a slit 88 that extends from the spilt 84 of the tubular sleeve 78 to the outer edge 90 of the panel. In this way, a pipe or conduit (which may for example already be connected to the patient) can be passed into the enclosure, so as to exit through the sleeve 78, without disconnecting either end.

After the conduit has been, properly positioned, the reinforced sleeve rim 82 is twisted around and squeezed into engagement with the conduit (not shown in the Figure), and pressed against the Velcro type pads 86. The rim 82 is then attached to the pads, locating the conduit tightly in position. It will be appreciated that this closure system works equally well for a wide range of conduit sizes. In addition, if any particular aperture 76 is not needed, the sleeve 78 can be twisted up more tightly to close the aperture completely (as indicated schematically in FIGS. 3a, 3b, 3c, 3d and FIGS. 4a, 4b, and 4c).

It will be appreciated that the slit 88 (shown in FIG. 5a) is also provided with suitable Velcro type or similar closure means along its adjacent edges, so that the entire closure can be made substantially leak proof, thus reducing significantly the overall re-circulation losses in the system.

Although the foregoing specific details describe various embodiments of the invention, persons reasonably skilled in the art will recognize that various changes may be made in the details of the method and apparatus of this invention without departing from the spirit and scope of the invention as defined in the appended claims. Therefore, it should be understood that, unless otherwise specified, this invention is not to be limited to the specific details shown and described herein.

We claim:

1. An apparatus for cooling a patient to a temperature below normal body temperature, the apparatus comprising:
   a patient-enclosing air tent having an inlet and outlet connected to an air-cooling system, the air-cooling system re-circulating air through the air tent to conserve energy;
   a plurality of sets of interleaved air bags collectively forming a patient supporting surface, each set of interleaved air bags being independently inflatable; and
   a high air pressure source in fluid communication with the air bags;
   wherein the high air pressure source is operable to alternately inflate the sets of interleaved air bags to periodically relieve alternately regions of the patient's body from pressure.

2. The apparatus of claim 1, further comprising:
   a fluid connection between the air bags and the air cooling system, wherein the air bags are operable to be pressurized with either relatively low pressure cold air which assists in cooling the patient but provides relatively little support or with relatively high pressure air which is sufficient to support the patient but which provides relatively less cooling effect.

3. The apparatus of claim 1, further comprising an aperture on the air tent for removable conduits, the aperture comprising a radially-collapsible sleeve of flexible material with a ring of hook or loop attachment material around its outer edge, and corresponding loop or hook material positioned on the surface of the enclosure around the base of the sleeve, the sleeve being operable to be tightened around the conduit by twisting the sleeve, and the hook or loop attachment of the outer edge being operable to be pressed against the cooperating loop or hook material at the base to secure the sleeve in a position around the conduit.

4. An apparatus for cooling a patient to a temperature below normal body temperature, the apparatus comprising:
   a patient-enclosing air tent having an inlet and outlet connected to an air-cooling system, the air-cooling system re-circulating air through the air tent to conserve energy;
   a plurality of air bags collectively forming a patient supporting surface;
   a high air pressure source in fluid communication with the air bags; and
   a fluid connection between the air bags and the air cooling system, wherein the air bags can be pressurized with either relatively low pressure cold air which assists in cooling the patient but provides relatively little support or with relatively high pressure air which is sufficient to support the patient but which provides relatively less cooling effect.

5. The apparatus of claim 4, further comprising an aperture on the air tent for removable conduits, the aperture comprising a radially-collapsible sleeve of flexible material with a ring of hook or loop attachment material around its outer edge, and corresponding loop or hook material positioned on the surface of the enclosure around the base of the sleeve, the sleeve being operable to be tightened around the conduit by twisting the sleeves, and the hook or loop attachment of the outer edge being operable to be pressed against the cooperating loop or hook material at the base to secure the sleeve in a position around the conduit.

6. An apparatus for cooling a patient to a temperature below normal body temperature, the apparatus comprising:
   a patient-enclosing air tent having an inlet and outlet connected to an air-cooling system, the air-cooling system re-circulating air through the air tent to conserve energy;
   at least one aperture on the air tent for removable conduits, the aperture comprising a sleeve of flexible material operable to be tightened around a conduit by twisting the sleeve so that it collapses radially about the conduit.

7. The apparatus of claim 6, wherein when no conduit is present, the sleeve is operable to be twisted tightly enough to close the aperture completely.

8. The apparatus of claim 6, further comprising a ring of resilient material to reinforce an outer edge of the sleeve.

9. The apparatus of claim 8, further comprising an attachment of hook or loop material around the outer edge of the sleeve and corresponding loop or hook material positioned on the surface of the air tent around the base of the sleeve, so that when the sleeve is tightened around the conduit by twisting the sleeve, the hook or loop attachment of the outer edge is operable to be pressed against the cooperating loop or hook material at the base to secure the sleeve in a position around the conduit.

10. An apparatus for cooling a patient to a temperature below normal body temperature, the apparatus comprising:
    a plurality of air bags collectively forming a patient supporting surface;

a high-pressure air source in fluid connection with the air bags, the high-pressure air source operable to provide sufficient air pressure to support the patient;

an air-cooling system in fluid connection with the air bags, the air-cooling system operable to provide relatively low pressasure cold air to cool the patient; and a fluid connection between the air bags and the air cooling system, wherein the air bags are operable to be pressurized with either relatively low pressure cold air which assists in cooling the patient but provides relatively little support or with relatively warmer high pressure air which is sufficient to support the patient but which provides relatively less cooling effect;

wherein the plurality of air bags comprise at least two sets of interleaved air bags, each set of interleaved air bags being independently inflatable; wherein each set is operable to be alternately supplied with relatively low pressure cold air or relatively warm high pressure air while another set is supplied with relatively warm high pressure air, or relatively low pressure cold air, in successive alternate cycles of operation, in order to both cool the patient and periodically relieve alternate regions of the patient's body from pressure.

11. An apparatus for cooling a patient to a temperature below normal body temperature, the apparatus comprising:

a plurality of air bags collectively forming a patient supporting surface;

a high-pressure air source in fluid connection with the air bags, the high-pressure air source operable to provide sufficient air pressure to support the patient;

an air-cooling system in fluid connection with the air bags, the air-cooling system operable to provide relatively low pressure cold air to cool the patient;

a fluid connection between the air bags and the air cooling system, wherein the air bags are operable to be pressurized with either relatively low pressure cold air which assists in cooling the patient but provides relatively little support or with relatively warmer high pressure air which is sufficient to support the patient but which provides relatively less cooling effect; and an air tent being supplied with cooled air from the same air-cooling system that is in fluid connection with the air bags.

12. An apparatus for treating a patient, the apparatus comprising an air tent for enclosing a patient and at least one aperture for carrying conduits through the air tent to the patient, the aperture comprising a sleeve of flexible material operable to be tightened around a conduit by twisting the sleeve so that it collapses radially about the conduit.

13. The apparatus of claim 12, wherein when no conduit is present, the sleeve is operable to be twisted tightly enough to close the aperture completely.

14. The apparatus of claim 12, further comprising a ring of resilient material to reinforce an outer edge of the sleeve.

15. The apparatus of claim 14, further comprising an attachment of hook or loop material around the outer edge of the sleeve and corresponding loop or hook material positioned on the surface of the air tent around the base of the sleeve, so that when the sleeve is tightened around the conduit by twisting the sleeve, the hook or loop attachment of the outer edge is operable to be pressed against the cooperating loop or hook material at the base to secure the sleeve in a position around the conduit.

16. The apparatus of claim 12, the air tent comprising a plurality of panels of flexible fabric material, the sleeve having a spilt and being mounted in one of the panels with a slit in the panel formed between the split of the sleeve and the edge of the panel to facilitate introduction of the conduit into the sleeve.

\* \* \* \* \*

UNITED STATES PATENT AND TRADEMARK OFFICE
CERTIFICATE OF CORRECTION

PATENT NO.   : 6,945,987 B2
DATED        : September 20, 2005
INVENTOR(S)  : Mark Beard et al.

It is certified that error appears in the above-identified patent and that said Letters Patent is hereby corrected as shown below:

Column 5,
Line 56, replace "alternately" with -- alternate --.

Column 6,
Line 34, replace "sleeves" with -- sleeve --.

Signed and Sealed this

Twenty-seventh Day of December, 2005

JON W. DUDAS
*Director of the United States Patent and Trademark Office*